(12) United States Patent
Gladman et al.

(10) Patent No.: US 8,110,717 B2
(45) Date of Patent: Feb. 7, 2012

(54) CARBOXYMETHYLATED CELLULOSIC WOUND DRESSING GARMENT

(75) Inventors: June Michaela Gladman, Warrington (GB); Bryan Griffiths, Chester (GB)

(73) Assignee: ConvaTec Technologies Inc., Las Vegas, NV (US)

( * ) Notice: Subject to any disclaimer, the term of this patent is extended or adjusted under 35 U.S.C. 154(b) by 649 days.

(21) Appl. No.: 11/427,899

(22) Filed: Jun. 30, 2006

(65) Prior Publication Data

US 2007/0042025 A1 Feb. 22, 2007

(30) Foreign Application Priority Data

Jul. 1, 2005 (GB) .................................. 0513555.3

(51) Int. Cl.
*A61F 13/00* (2006.01)
(52) U.S. Cl. ............ 602/48; 602/43; 424/443; 424/446; 424/447
(58) Field of Classification Search .................. 424/443, 424/446, 447; 602/43, 48
See application file for complete search history.

(56) References Cited

U.S. PATENT DOCUMENTS

| | | | |
|---|---|---|---|
| 1,641,101 A | | 8/1927 | Scott |
| 6,075,177 A | * | 6/2000 | Bahia et al. ................ 602/43 |
| 6,548,728 B1 | * | 4/2003 | Faries et al. ................ 602/42 |
| 6,548,730 B1 | | 6/2006 | Patel |
| 2004/0106344 A1 | | 6/2004 | Looney |

FOREIGN PATENT DOCUMENTS

| | | |
|---|---|---|
| EP | 1378255 | 1/2004 |
| GB | WO 93/12275 | 6/1993 |
| GB | WO 94/16746 | 8/1994 |
| GB | WO 00/01425 | 1/2000 |
| GB | 2357286 | 6/2001 |
| GB | WO 02/43743 | 6/2002 |
| GB | WO 03/092755 | 11/2003 |
| WO | WO03092755 | 11/2003 |
| WO | WO2004062701 | 7/2004 |

OTHER PUBLICATIONS

Bray, "Carboxymethylated Cellulosic Wound Dressing", Nov. 13, 2003, International Application Published Under the PCT, WO 03/092755.*

Other: In accordance with 37 C.F.R. § 1.98 (a)(2)(iii), Applicants wish to call the Examiner's attention to the related pending application filed on Jun. 30, 2006, entitled "Wound Dressing Material", U.S. Appl. No. 11/427,884.

* cited by examiner

*Primary Examiner* — Karlheinz R Skowronek
*Assistant Examiner* — Ali Soroush
(74) *Attorney, Agent, or Firm* — John M. Kilcoyne

(57) ABSTRACT

A body shaped wound dressing wherein the dressing is a knitted or woven garment comprising a cellulosic yarn, which garment has been carboxymethylated at least in parts of its wound contacting surface.

11 Claims, 4 Drawing Sheets

CARBOXYMETHYLATED CELLULOSIC WOUND DRESSING GARMENT

This invention relates to wound dressings of the type in which the wound-contacting surface is composed of a cellulosic material that has been subjected to carboxymethylation. In particular, the invention relates to carboxymethylated dressings used in the treatment of burns or skin graft sites.

BACKGROUND OF THE INVENTION

It is known to provide wound dressings composed of certain materials in the form of a three dimensional shape complementary to the shape of a body part. For example, GB 2357286 discloses a process for preparing a shaped polyurethane article for use as or in a wound dressing, for example, a glove dressing for a whole hand, in which a last having the desired three-dimensional shape is provided, an aqueous layer is applied over the last, a layer of an isocyanate-capped prepolymer is applied over the last to react with the aqueous layer and form a polyurethane foam layer, which is then stripped from the last.

WO 03/092755 describes wound dressings in the form of body-shaped components composed of body-shaped cellulosic fabric which has been carboxymethylated at the wound contacting surface. The body shaped component composed of a fabric comprising a cellulosic material is subjected to a carboxymethylation process to carboxymethylate the cellulosic material at the wound-contacting surface. Prior to this disclosure it had not been suggested to provide body-shaped wound dressings incorporating a carboxymethylated cellulosic fabric. This may well have been because it can be difficult to create a body-shaped wound dressing from carboxymethylated cellulosic fiber because of the inherent weakness of such fiber which may preclude normal knitting into body shaped format such as gloves, and because of the need to keep the fiber dry during processing to stop it from absorbing moisture and becoming sticky.

Burns in difficult to dress areas such as the face, hands and upper torso are currently treated in a variety of ways which do not provide an ideal solution to the special problems presented by such wounds. For example, a burn to the hand is generally treated by covering the hand in antibacterial cream and putting it in a plastic bag secured around the wrist with a bandage and tape. Such treatment allows the patient to move the fingers freely but has the disadvantages that exudate from the wound collects in the bag which looks unsightly and may become heavy, dragging across the burn surface and making mobilization difficult. The skin on the hand also becomes very macerated making the wound difficult to assess.

Burns on the face are generally treated using dressings which are flat but flexible. The difficulty arises in maintaining contact between the wound and the dressing in a highly contoured area such as the nose, cheek or chin. Taping of the dressing is not always possible especially where the intact skin is fragile and secondary dressing with, for instance, a bandage may not increase conformity with the wound. It may also be difficult to manage the exudate produced by the wound in such an area and pooling or strike through may occur.

Wounds to an extensive area such as the chest are presently treated using many overlapping patch type dressings which are difficult to maintain in contact with the wound due to the problems of fixation and contraction. Many wound dressings contract on the absorption of exudate and, hence, where it is not possible to cover the wound with one dressing, that contraction needs to be allowed for by overlapping the dressings. This then presents a problem in fixing the dressings and maintaining contact with the wound.

SUMMARY OF THE INVENTION

The present invention, therefore, seeks to provide improved wound dressings in the form of body shaped garments which mitigate the problems associated with present dressings and methods of manufacturing them.

We have now found that it is possible to knit body shaped garments from a yarn comprising a cellulosic fiber such that the garments can be carboxymethylated, at least at the wound contacting surface, after being knitted.

Accordingly, the invention provides a body-shaped wound dressing characterized in that the dressing is a knitted or woven garment comprising a cellulosic yarn which garment has been carboxymethylated at least in parts of its wound contacting surface.

Such garments are ideal dressings for highly contoured areas such as the face and hands and can easily be placed in intimate contact with the wound and surrounding skin. As the knitted garment can be dimensioned so that the garment is in mild extension when in place on the patient, the garment is maintained in contact with the wound. The flexibility of the knitted structure allows the patient mobility of the wounded area, for example mobility of the fingers.

DETAILED DESCRIPTION OF THE INVENTION

Figure 1:
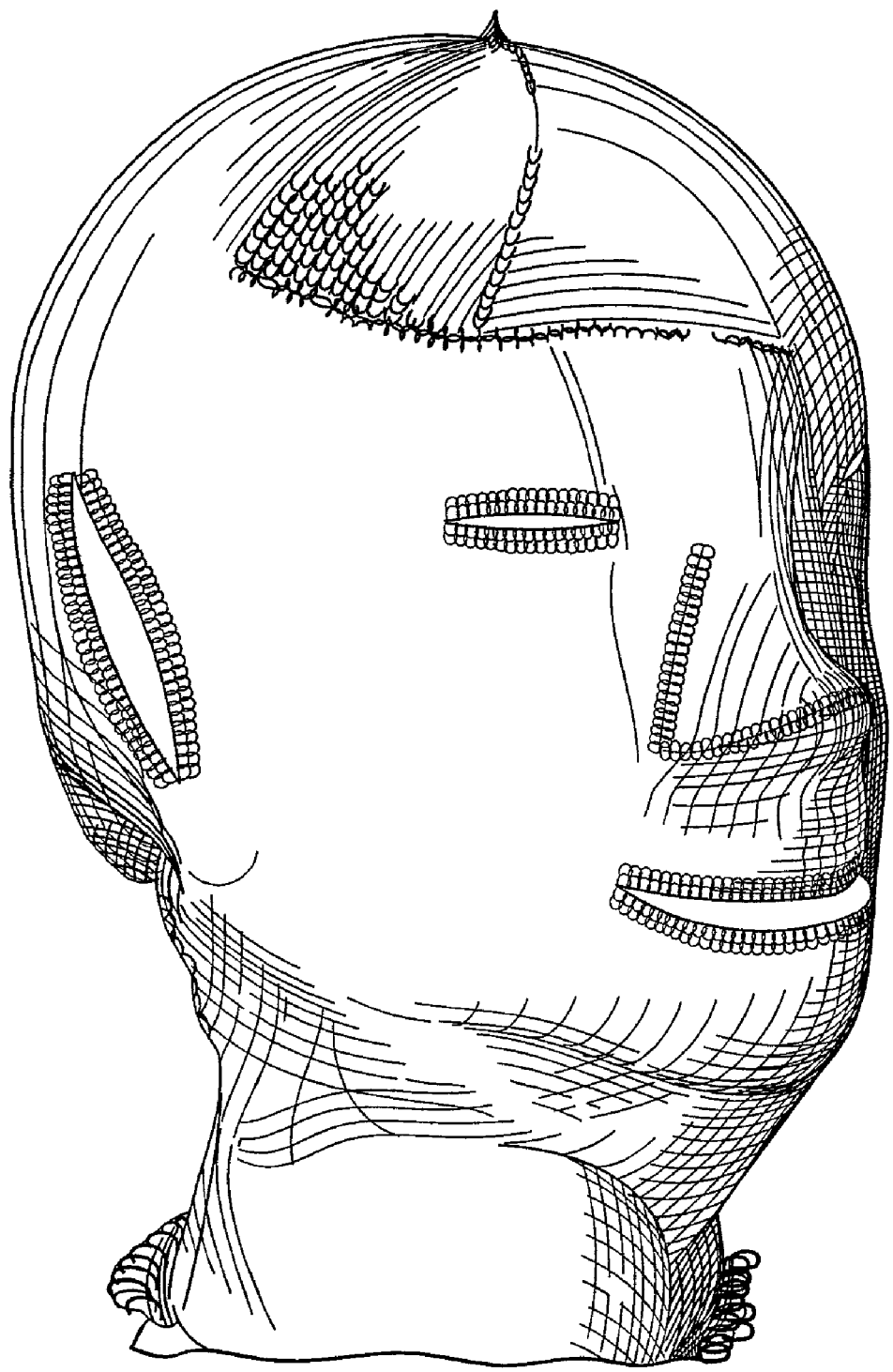
FIG. 1 is a front perspective view of a head mask according to the invention.

Preferably, the wound dressing is comprised of a cellulosic yarn and a textile yarn that is non-cellulosic. This allows the cellulosic yarn to be incorporated in those areas of the garment where absorbency is required, while the non-cellulosic yarn can be incorporated in those areas where absorbency is not required. The non-cellulosic yarn will not be carboxymethylated when the garment is subjected to carboxymethylation and can, for example, be any yarn able to withstand the carboxymethylation process and subsequent gamma irradiation, for instance, nylon, polyolefin, polyamide or lycra. Carboxymethylation is preferably carried out by the method described in WO 03/092755.

Preferably, the knitted garment is comprised of a wound contacting surface knitted from a cellulosic yarn and an outer surface knitted from a textile yarn. In this manner, the garment has an inner surface which gels on contact with exudate and an outer surface which does not gel, but remains as a knitted structure, much like a conventional secondary dressing. This has the advantage that the garment may not require a secondary dressing to keep it in place and the outer knitted textile layer would give the garment sufficient integrity to be removed from the wound in one piece without portions of the garment being shed into the wound.

The garment may be comprised of areas of plain knitting, ribbing or other stitch patterns in order to build into the garment elasticity, flexibility or high and low tension. The garment may, for instance, comprise lycra in those regions where mobility is required, for example the fingers.

The garment may be in any form including the form of a head mask, a glove, with or without fingers, or a vest.

The cellulosic yarn may be made of a mixture of cellulosic and non-cellulosic fibers, provided that an appropriate degree of carboxymethylation is achieved in the required parts.

The garment may additionally include one or more medicaments. For example, an antimicrobial agent, an antibiotic, an anesthetic, an anti-inflammatory agent, a skin protective agent or an odor absorbing agent or any combination thereof may be incorporated in the garment. Suitable antimicrobial agents can include silver or silver containing compounds and can be incorporated in carboxymethylcellulosic fibers, for example by the method of WO 02/43743. One method comprises preparing a solution of an organic solvent and a source of silver, placing the carboxymethylated garment in the solution for a sufficient time to incorporate silver in the fibers and placing the garment in a solution of a binding agent, for example, ammonium chloride.

Carboxymethylation can be achieved, for example, by sequential or simultaneous treatment of the cellulosic material with a strong alkali, such as aqueous sodium hydroxide, and monochloroacetic acid or a salt thereof. The appropriate reaction conditions will depend upon the composition of the fabric and the degree of carboxymethylation required and will be readily apparent to the person skilled in the art. They may be identical or similar to those described in WO 93/12275, WO 94/16746 or WO 00/01425 to which the reader is directed for further detail.

Preferably, the carboxymethylation is carried out in the presence of industrial methylated spirits (IMS), and IMS is, preferably, also used in a subsequent washing step, suitably along with water, as a cleaner and sterilizer. The degree of carboxymethylation is preferably such that upon absorption of exudate the fibers at the skin-contacting surface of the body-shaped component form a gel.

A further aspect of the invention provides a method of manufacturing a body shaped wound dressing that is a knitted garment comprising a cellulosic yarn and has been obtained by:
  (i) knitting a garment comprising a cellulosic yarn; and
  (ii) carboxymethylating the garment to carboxymethylate the cellulosic yarn at least in parts of its wound contacting surface.

Figure 2:
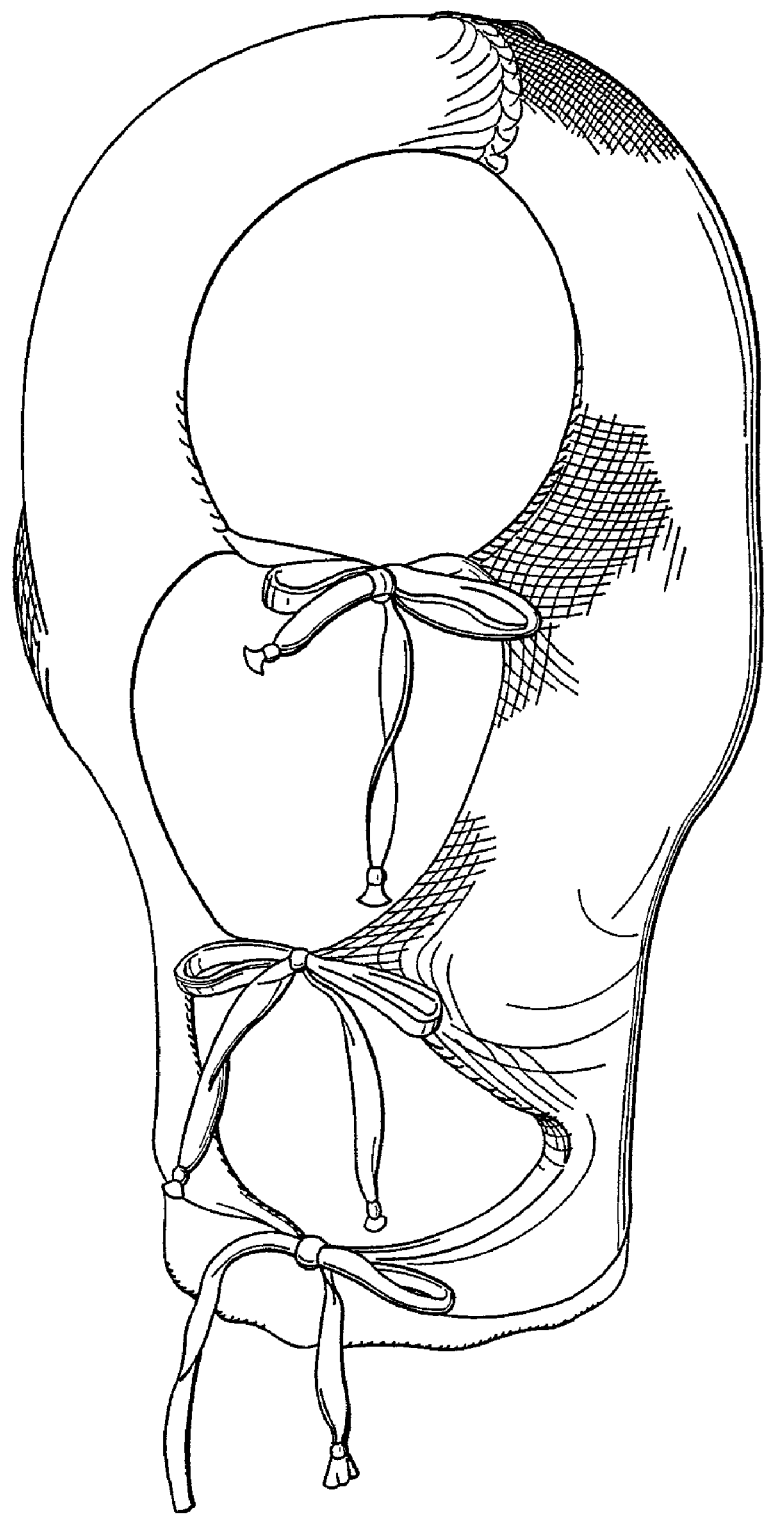
FIG. 2 is a rear perspective view of a head mask according to the invention.

FIG. 1 shows a head mask according to one aspect of the invention. The head mask has been knitted from a cellulosic yarn and a textile (non-cellulosic) yarn on a plating machine, in particular, by cross-plating such that the cellulosic yarn (e.g., Lyocell) forms the inner, wound contacting ply of the mask and the non-cellulosic yarn forms the outer ply of the mask. The plys are joined together at regular intervals by stitches that cross from one ply to the other so that the garment is a coherent whole. The mask has slits formed at the eyes, mouth and ears and has substantial shaping at the nose, jaw, eyes, ears and cranium so that close conformity is maintained with the wound and skin. FIG. 2 shows the rear of the mask and, in particular, the fastening in the form of ties. The mask may be fastened by hook and loop fastenings or a lace. The ear and eye slits enable these areas to be additionally treated, if necessary. Once the garment has been knitted, the whole garment is carboxymethylated to carboxymethylate the cellulosic yarn at the wound contacting surface. The garment is then packaged and sterilized, for example, by gamma irradiation. It is envisaged that the mask be available in several sizes and, generally, oversized to allow for burn trauma.

Figure 3:
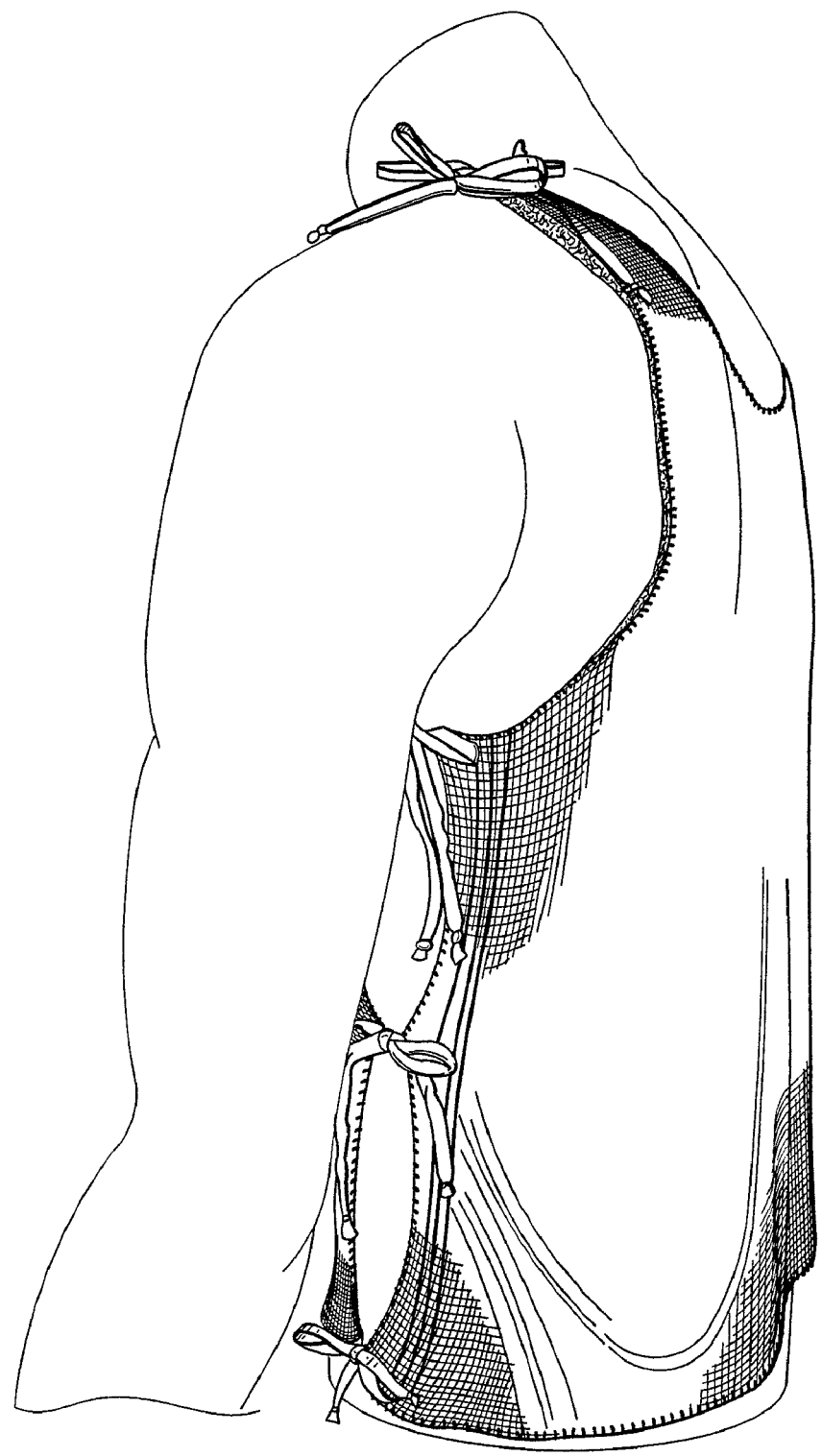
FIG. 3 is a side view of a vest according to the invention.

FIG. 3 shows a vest according to the invention. The vest has been knitted from a cellulosic yarn (e.g., Lyocell) and a non-cellulosic yarn (polyester) on a plating machine, in particular, by cross-plating such that the cellulosic yarn forms the inner ply of the vest and the polyester forms the outer ply of the vest. The plys are joined together at regular intervals by stitches that cross the plys so that the garment is a coherent whole. The vest has ties at the shoulder and sides so that the garment can be kept in close conformity with the wound and surrounding skin. Alternatively, the vest can be fastened by hook and loop fastenings. Once the garment has been knitted, the whole garment is carboxymethylated to carboxymethylate the cellulosic yarn at the wound contacting surface. The garment is then packaged and sterilized, for example, by gamma irradiation.

Figure 4:
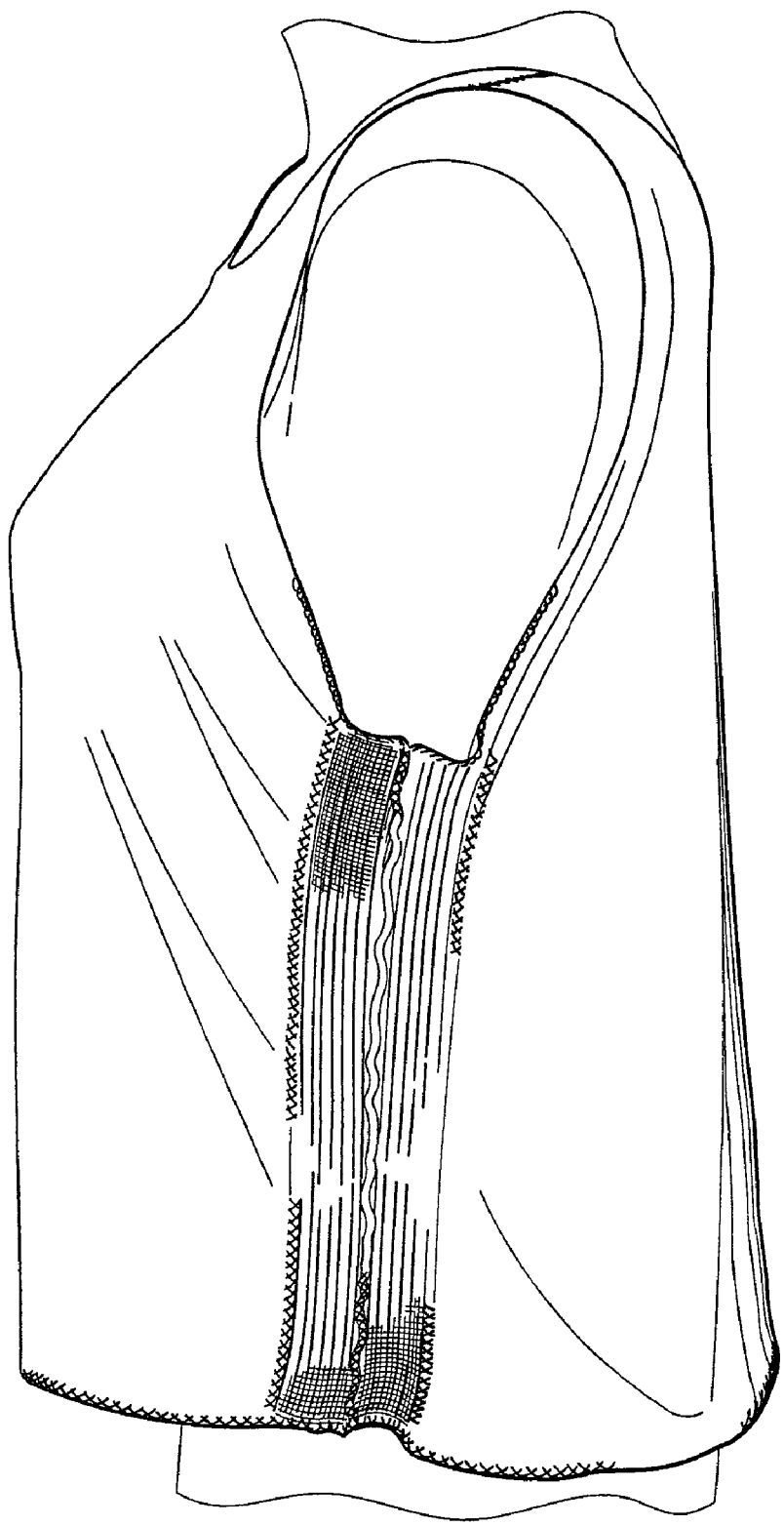
FIG. 4 is a side view of an alternative vest according to the invention.

FIG. 4 shows an alternative embodiment of the vest of FIG. 3 where the vest is seamed at the shoulder and sides by outward facing seams. Such seams reduce potential irritation to the patient. The side of the vest is characterized by an area of ribbing that confers elasticity on the vest and enables close conformity between the vest and the wound and skin.

The invention claimed is:

1. A body shaped wound dressing wherein the dressing is a knitted garment comprising a wound contacting surface knitted from a cellulosic yarn and an outer surface knitted from a textile yarn, which garment has been carboxymethylated at least in parts of its wound contacting surface and is dimensioned so that the garment is in mild extension when worn by a patient.

2. The body shaped wound dressing as claimed in claim 1 wherein the textile yarn is nylon or polyolefin.

3. The body shaped wound dressing as claimed in claim 1 wherein the garment has areas of ribbed knitting.

4. The body shaped wound dressing as claimed in claim 1 wherein the garment has areas of knitting in different tensions.

5. The body shaped wound dressing as claimed in claim 1 wherein the garment is a head mask with shaping to conform to a patient's nose and with slits for eyes, mouth and ears.

6. The body shaped wound dressing as claimed in claim 1 wherein the garment is a glove with fingers.

7. The body shaped wound dressing as claimed in claim 1 wherein the garment is a glove without fingers.

8. The body shaped wound dressing as claimed in claim 1 wherein the garment is a vest.

9. A method of manufacturing a body shaped wound dressing wherein the dressing is a knitted garment comprising a cellulosic yarn, said method comprising:
  i. knitting a garment comprising a wound contacting cellulosic yarn and an outer surface knitted from a textile yarn; and
  ii. carboxymethylating the garment to carboxymethylate the cellulosic yarn at least in parts where the garment would contact a wound.

10. The method as claimed in claim 9 further comprising placing the garment in a solution of a source of silver in an organic solvent for sufficient time to incorporate silver in the fibers.

11. A method of treating a burn comprising applying to the burn, the body-shaped wound dressing of claim 1.

* * * * *